United States Patent [19]

Vasta

[11] 4,340,741

[45] Jul. 20, 1982

[54] PROCESS FOR MAKING VINYL OXAZOLINE DRYING OIL ESTERS

[75] Inventor: Joseph A. Vasta, Wilmington, Del.

[73] Assignee: E. I. Du Pont de Nemours and Company, Wilmington, Del.

[21] Appl. No.: 211,584

[22] Filed: Dec. 1, 1980

[51] Int. Cl.$^3$ .................................... C07D 263/14
[52] U.S. Cl. ............................................. 548/237
[58] Field of Search ................................... 548/237

[56] References Cited

U.S. PATENT DOCUMENTS

| | | | |
|---|---|---|---|
| 3,248,397 | 4/1966 | Purcell | 260/307 |
| 3,523,123 | 8/1970 | Wehrmeister | 548/237 |
| 3,654,229 | 4/1972 | Hunsucker | 548/237 |
| 4,147,674 | 4/1979 | Vasta | 260/17 R |

FOREIGN PATENT DOCUMENTS 1134050 11/1968 United Kingdom.

OTHER PUBLICATIONS

Brochure Oxazolines by Commercial Solvents Corp. pp. 1-30, 1969.

*Primary Examiner*—Donald G. Daus
*Assistant Examiner*—Sharon A. Gibson
*Attorney, Agent, or Firm*—Hilmar L. Fricke

[57] ABSTRACT

An improved process for preparing a vinyl oxazoline drying oil ester by reacting drying oil fatty acids with tris(hydroxy methyl) amino methane to form an intermediate which is further reacted at about 175°-190° C. with a formaldehyde/alcohol solution to form the vinyl oxazoline drying oil ester; the improvement used with this process is the use of at least 3 moles of formaldehyde to one mole of intermediate and about 1-5% by weight, based on the weight of the intermediate, of methanol and adding after the reaction with formaldehyde about 5-25% by weight, based on the weight of the ester solution, of an alcohol, a ketone or a mixture of an alcohol and a ketone; polymers of this ester and coating compositions of these polymers are also disclosed.

7 Claims, No Drawings

PROCESS FOR MAKING VINYL OXAZOLINE DRYING OIL ESTERS

BACKGROUND OF THE INVENTION

This invention is related to a process for preparing vinyl oxazoline drying oil esters and in particular to an improved process for preparing such esters.

A process for preparing vinyl oxazoline drying oil esters is disclosed in Purcell U.S. Pat. No. 3,248,397 issued Apr. 26, 1966. The process as taught in the patent provides esters with a relatively low vinyl content. Dimers and oligomers of these esters also are formed in the process. These dimers and oligomers often cause gelation and seed formation in polymers formed with these esters. Polymers prepared with esters having a low vinyl content when formulated into coating compositions have a lower level of exterior durability and are subject to cracking. There is a need for an improved process that prepares vinyl oxazoline drying oil esters having a high vinyl level and do not contain dimers or oligomers.

SUMMARY OF THE INVENTION

An improved process for preparing a vinyl oxazoline drying oil ester which comprises reacting at about 150°-225° C., in the presence of a solvent, drying oil fatty acids with this(hydroxymethyl) amino methane to form an intermediate, the intermediate is then reacted at about 175°-190° C. with a formaldehyde alcohol solution to form a solution of a vinyl oxazoline drying oil ester of the formula

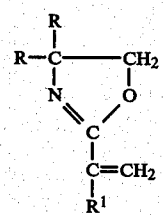

where R is

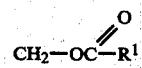

and $R^1$ is the residue of a drying oil fatty acid; the improvement that is used with the above process comprises the use of at least 3 moles of formaldehyde to one mole of intermediate and about 1-5% by weight, based on the weight of the intermediate, of methanol and adding after the reaction with formaldehyde about 5-25% by weight, based on the weight of the ester solution, of an alcohol having 1-6 carbon atoms, a ketone or a mixture of an alcohol and a ketone.

DESCRIPTION OF THE INVENTION

The improved process of this invention forms a vinyl oxazoline drying oil ester in which at least 60% and preferably 80-100% of the esters have vinyl groups. Polymers made from these esters when formulated into coating compositions provide finishes with excellent outdoor durability in comparison to finishes formulated from such polymers that utilize vinyl oxazoline drying oil esters which have a low vinyl content.

Also, in the process of this invention oligomers and dimers of the vinyl oxazoline drying oil esters are not formed. Gelation and seed formation are not present to any substantial extent in polymers formulated from vinyl oxazoline esters of the improved process.

In the improved process, an amino hydroxy compound such as tris(hydroxymethyl) amino methane is reacted with drying oil fatty acids in the presence of solvent at about 150°-225° C. for about 1-4 hours to form an intermediate of oxazoline drying oil ester.

Typical drying oil fatty acids are soya oil fatty acids, linseed oil fatty acids, tall oil fatty acids, tung oil fatty acids, safflower oil fatty acids, poppy seed oil fatty acids and the like. These acids contain mixtures of $C_{18}$ unsaturated fatty acids such as linoleic acid, linolenic acid and oleic acid. Other acids that can be used are dodecanoic acid, ricinoleic acid, licanic acid, arachidonic acid, behenic acid, erucic acid, clupanodonic acid, lignoceric acid and nisinic acid.

The oxazoline drying oil ester has the following formula:

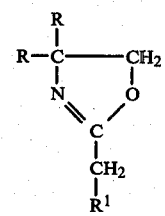

where R and $R^1$ are as defined above.

The improvement that is used with the above process to form esters in which at least 60% and preferably 80-100% of the esters contain a vinyl group is the reaction of the intermediate of the oxazoline drying oil ester with at least a 3/1 molar excess of formaldehyde to ester. Generally, about 3.2 to 4.0 moles of formaldehyde are used per mole of oxazoline drying oil ester. A formaldehyde methanol mixture is used. About 1-5% by weight, based on the intermediate, of methanol is used. Reaction temperature is the same as above and reaction time is about 1-5 hours. Preferably, a reaction temperature of 180°-190° C. is used to obtain a high conversion.

Formaldehyde compounds such as paraformaldehyde and formaldehyde releasing substances such as trioxane also can be used.

The presence of methanol in the reaction reduces and essentially eliminates any build-up of paraformaldehyde in a condenser used in the process for making the ester. The methanol either can be added with the formaldehyde or introduced into the top of a condenser used in the reaction.

After the reaction is complete, a solvent of alcohol having 1-6 carbon atoms, ketone or a mixture of the above is added to the vinyl oxazoline drying oil ester solution to cool the ester solution below 140° C. Below 140° C. no further reaction will occur. About 5-25% by weight, based on the weight of the ester solution, of the solvent is added. The solvent can be chilled to rapidly reduce the temperature of the solution.

Typical alcohols that can be used are methyl alcohol, butyl alcohol, isobutyl alcohol, pentyl alcohol, hexyl alcohol and the like. Typical ketones are acetone, methyl ethyl ketone, methyl isobutyl ketone, methyl amyl ketone and the like.

The cooling of the ester solution reduces the formation of dimers and oligomers of the vinyl oxazoline drying oil esters.

Vinyl oxazoline drying oil esters made according to the process of this are readily polymerized with ethylenically unsaturated monomers as taught in Vasta U.S. Pat. No. 4,147,674 issued Apr. 3, 1979 which is incorporated by reference.

Typical useful polymers which are used to form high quality coating compositions are as follows:

(1) a polymer of about 22–28% by weight of styrene, about 22–28% by weight methyl methacrylate, about 37–43% by weight of a vinyl oxazoline drying oil ester (described above) where R and $R^1$ are from soya oil fatty acids, about 3–7% by weight of lauryl methacrylate and about 3–7% by weight of acrylic acid;

(2) a polymer of about 22–28% by weight of styrene, about 22–28% by weight methyl methacrylate, about 37–43% by weight of a vinyl oxazoline drying oil ester (described above) where R and $R^1$ are from linseed oil fatty acids and about 8–12% by weight acrylic acid; or (3) a polymer of about 22–28% by weight of styrene, about 22–28% by weight methyl methacrylate, about 37–43% by weight of a vinyl oxazoline ester (described above) where R is from soya oil fatty acids and about 8–12% by weight of acrylic acid.

The following example illustrates the invention. All parts and percentages are on a weight basis unless otherwise indicated:

EXAMPLE I

An oxazoline drying oil ester is prepared by charging the following constituents into a reaction vessel equipped with a stirrer, reflux condenser, or heating mantle and a nitrogen inlet.

|  | Parts by Weight |
|---|---|
| Soya oil fatty acids | 835.00 |
| Tris(hydroxymethyl) amino methane | 129.30 |
| Toluene | 26.03 |
| Total | 990.33 |

The constituents are heated under a nitrogen blanket and distillate is removed as follows:

| Total Reaction Time (Min) | Temp. (°C.) | Distillate Removed |
|---|---|---|
| 35 | 125 | — |
| 55 | 155 | 11.17 |
| 65 | 160 | 20.06 |
| 82 | 162 | 30.50 |
| 98 | 173 | 43.50 |
| 130 | 175 | 51.50 |
| 240 | 210 | 66.30 |
| 370 | 215 | 71.50 |
| 400 | 215 | 73.94 |

The resulting ester has an acid number of about 4.31.

A vinyl oxazoline drying oil ester then is prepared by charging the following constituents into a reaction vessel equipped as above:

|  | Parts by Weight |
|---|---|
| Portion 1 | |
| Drying oil oxazoline ester (prepared above) | 406.0 |
| Portion 2 | |
| Butyl Formcel (40% solution of formaldehyde in n-butanol) | 110.8 |
| Portion 3 | |
| Methyl alcohol | 24.8 |
| Total | 541.6 |

Portion 1 is charged into the reaction vessel and heated to about 185°–190° C. Portion 2 is added at a uniform rate over a 120 minute period. Simultaneously with portion 2, portion 3 is added at a uniform rate over a 165 minute period while maintaining the reaction temperature at about 185°–190° C. After the addition of portion 3, heat is turned off and the resulting composition is cooled to room temperature.

The composition contains 78% of nonvolatile solids oxazoline drying oil ester and has a relative viscosity measured at 25° C. of 1.019. Gel permeation chromatography (GPC) data indicates that about 90% of the esters have a vinyl group.

Polymer A is prepared using the same constituents and polymerization procedure as in Example 1 of U.S. Pat. No. 4,147,674 with the above prepared 90% oxazoline drying oil ester. White mill base A and white paint A are prepared from this polymer using the same constituents as in Example 1 of the above patent except polymer A is used. The resulting paint is sprayed onto phosphatized steel parts and dried at room temperature.

A vinyl oxazoline drying oil ester is prepared using the above constituents and reaction conditions except a 1:1 molar ratio of formaldehyde to drying oil oxazoline ester is used. The resulting composition has only about 30% of the ester containing vinyl groups as determined by GPC data.

Polymer B is prepared using the same constituents and polymerization procedure as in Example 1 of the above '674 patent with the above prepared 30% vinyl drying oil oxazoline ester. White mill base B and white paint B are prepared from this polymer using the same constituent as in Example 1 of the above patent except polymer B is used. The resulting paint is sprayed onto phosphatized steel panels and dried at room temperature.

The panels were exposed in Florida facing South at a 45 degree angle. The panels coated with paint A showed substantially less degradation from weathering than the panels coated with paint B. This is an expected result since paint A was formulated from a polymer containing a high vinyl content vinyl oxazoline drying oil ester.

I claim:

1. An improved process for preparing a vinyl oxazoline drying oil ester which comprises reacting at about 150°–225° C., in the presence of solvent, drying oil fatty acids with tris(hydroxymethyl) amino methane to form an intermediate, said intermediate being further reacted at about 175°–190° C. with a formaldehyde alcohol solution to form a solution of a vinyl oxazoline drying oil ester of the formula

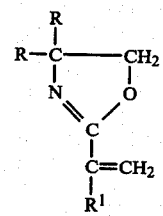

where R is

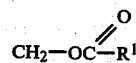

and $R^1$ is the residue of a drying oil fatty acid;
the improvement used therewith comprises the use of at least 3 moles of formaldehyde to one mole of intermediate and about 1–5% by weight, based on the weight of the intermediate of methanol and adding after the reaction with formaldehyde about 5–25% by weight, based on the weight of the ester solution, of an alcohol having 1–6 carbon atoms, a ketone having 3–7 carbon atoms or a mixture of said alcohol and ketone.

2. The process of claim 1 in which a mixture of methyl alcohol and methyl ethyl ketone is added to the ester solution.

3. The process of claim 1 in which the drying oil fatty acids used to prepare the ester are soya oil fatty acids.

4. The process of claim 1 in which the drying oil fatty acids used to prepare the ester are tall oil fatty acids.

5. The process of claim 1 in which the drying oil fatty acids used to prepare the ester are linseed oil fatty acids.

6. The process of claim 1 in which the drying oil fatty acids used to prepare the ester comprise a mixture of linoleic acid, linolenic acid and oleic acid.

7. The process of claim 1 in which the reaction with the formaldehyde alcohol solution is at about 180°–190° C.

* * * * *